(12) United States Patent
Meer et al.

(10) Patent No.: US 7,809,111 B2
(45) Date of Patent: Oct. 5, 2010

(54) USER CONTROL DEVICE FOR CONTROLLING A MEDICAL SYSTEM

(75) Inventors: Oliver Meer, München (DE); Martin Ramsauer, Pyrbaum (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 12/280,900

(22) PCT Filed: Feb. 22, 2007

(86) PCT No.: PCT/EP2007/051721

§ 371 (c)(1),
(2), (4) Date: Jan. 12, 2009

(87) PCT Pub. No.: WO2007/101793

PCT Pub. Date: Sep. 13, 2007

(65) Prior Publication Data
US 2009/0190715 A1 Jul. 30, 2009

(30) Foreign Application Priority Data
Mar. 6, 2006 (DE) .................. 10 2006 010 196

(51) Int. Cl.
*H05G 1/56* (2006.01)
(52) U.S. Cl. ........................ 378/114; 378/37
(58) Field of Classification Search .............. 378/37, 378/193, 195–197, 114–116, 204
See application file for complete search history.

(56) References Cited

U.S. PATENT DOCUMENTS

| | | | |
|---|---|---|---|
| 4,856,741 A * | 8/1989 | Schaefer | 248/122.1 |
| 5,322,084 A | 6/1994 | Ghiassian | 137/607 |
| 5,590,166 A | 12/1996 | Suni et al. | 378/37 |
| 5,679,110 A | 10/1997 | Hamazaki | 600/124 |
| 6,051,797 A | 4/2000 | Meinel | 200/86.5 |
| 6,234,672 B1 | 5/2001 | Tomasetti et al. | 378/197 |
| 2008/0069299 A1 | 3/2008 | Ramsauer | 378/62 |

FOREIGN PATENT DOCUMENTS

| | | |
|---|---|---|
| DE | 80 96 499.9 U1 | 11/1983 |
| DE | 84 34 499.7 U1 | 10/1986 |
| DE | 86 34 352.1 U1 | 4/1988 |

(Continued)

OTHER PUBLICATIONS

German Office Action dated Dec. 6, 2006 with English translation.

(Continued)

*Primary Examiner*—Courtney Thomas
(74) *Attorney, Agent, or Firm*—Brinks Hofer Gilson & Lione

(57) ABSTRACT

An operating device with an operating piece, which may be positioned near the floor, includes at least one operating element for controlling a medical instrument. Operation of the medical instrument is possible by actuation of the at least one operating element by foot, such that the operator has hands free to use for further manipulation. A flexible positioning of the operating piece in a defined movement range is possible by arrangement of the operating device such as to be pivotable and/or extendable/retractable relative to the medical instrument which is good for operational manipulation. The operational device may be used during operation of a mammography device.

20 Claims, 3 Drawing Sheets

FOREIGN PATENT DOCUMENTS

| | | |
|---|---|---|
| DE | 89 01 789.7 U1 | 3/1989 |
| DE | 197 26 234 A1 | 12/1998 |
| DE | 10 2004 034 238 A1 | 2/2006 |
| DE | 10 2004 034 240 A1 | 2/2006 |
| EP | 0273 276 A1 | 7/1988 |
| JP | 2001 046365 A | 2/2001 |

OTHER PUBLICATIONS

German Office Action dated Jan. 15, 2007 with English translation.
International Search Report dated Oct. 15, 2007 with English translation.
Written Opinion dated Oct. 15, 2007 with English translation.

* cited by examiner

USER CONTROL DEVICE FOR CONTROLLING A MEDICAL SYSTEM

The present patent document is a §371 nationalization of PCT application Ser. No. PCT/EP2007/051721, filed Feb. 22, 2007, designating the United States, which is hereby incorporated by reference. This patent document also claims the benefit of DE 10 2006 010 196.0, filed Mar. 6, 2006, which is also incorporated by reference.

BACKGROUND

The present embodiments relate to a user control device for controlling a medical system.

A medical system may be equipped with a user control device that has a user control part (unit) supported near the floor. The user control part can be operated with one foot. The person operating the equipment may use the user control device for further handling actions. The user part provides hands free operation for the person operating the equipment.

Mammography systems may include a user control device with a user control part. The user control device includes a user control part, supported near the floor, for controlling the mammography system and a cable connection with the mammography system. The user control elements, which are disposed on the user control part, may be used to control a height of a stage of the mammography system and a spacing of a compression joint of the mammography system relative to the stage. An equipment operator may position the object on the stage with his hands, and at the same time, adapt the height of the stage and the spacing of the compression joint from the stage to the particular patient to be examined with one foot. A user control device, with a cable connection to a floor plate of the mammography system, may be disposed on both the left and the right of the patient. The user control device may be accessed from both sides relative to the patient.

Because of the cable connection or cord, which connects the user control part of the user control device to the particular medical system, the user control part may be positioned flexibly. The operator may dispose the user control part in a position on the floor that assures that the operator's foot can easily reach it. The cord is subjected to mechanical stress because of frequent changes of position and because stepping on the cord is almost unavoidable. Because of the cord's position on the floor is difficult to control, the cord is a risk because someone might trip on it.

SUMMARY AND DESCRIPTION

The present embodiments may obviate one or more of the drawbacks or limitations inherent in the related art. For example, in one embodiment, a user control device, which is supported near the floor and has good accessibility for an equipment operator, makes operating the equipment possible with little wear and little hindrance.

The user control device for controlling a medical system has a dimensionally stable connecting part between the medical system and a user control part. The user control part can be supported near the floor, of the user control device. The user control part can be connected to the medical system with little wear and little hindrance. Because of the dimensionally stable embodiment of the connecting part, this part is exposed to less wear, compared to a conventional connection cord. The dimensional stability assures a position of the connecting part that is especially readily perceptible and easily controlled at all times, compared to a very poorly controllable position of a conventional connecting cord. The risk of tripping is reduced with the dimensionally stable connecting part. The connecting part makes it possible for the user control part to be in an exposed position relative to the medical system, so that the user control part is accessible to the operator.

At least one user control element for controlling the medical system is provided on the user control part. The user control part can be supported near the floor. The connecting part from the user control part to the medical system includes at least one signal line for transmitting control signals from the at least one user control element to the medical system. The at least one signal line provides secure transmission of the control signals. The control signals can be transmissible to the medical system in electrical or optical form, for example.

A signal line can be at least one electrical cable connection (cord), which disposed inside the connecting part. The cord is protected from mechanical stress by the dimensionally stable connecting part. The embodiment of the connecting part, which involves less effort and is more economical, allows the use of conventional cords as the at least one signal line.

The connecting part is a hollow shaft that receives the at least one signal line. The connecting part makes a signal connection possible with little effort and allows the signal line to be disposed inside the hollow shaft, for example, in a simple way. The signal line, for example, a conventional cord, can be supported without further locking in the hollow shaft that protects the cord against external mechanical stress. Alternatively, it is possible for the at least one signal line to be potted (connected) with the connecting part.

The user control part and the connecting part can be a one-piece unit. The one-piece unit makes especially simple production possible. The unit is stable mechanically and avoids connection seams that are vulnerable to becoming soiled.

The connecting part may be supported on the floor. Accordingly, the connecting part is braced by the floor. Alternatively, the connecting part is a connecting bridge that at least partially has spacing from the floor. The spacing from the floor reduces possible soiling of the connecting bridge and lessens wear from friction between the connecting bridge and the floor.

In one embodiment, the user control device is supportable on the medical system in such a way that it is pivotable relative to the medical system. Accordingly, the user control part can be disposed flexibly for better accessibility, for example, depending on the particular equipment operating situation and depending on preferences of the particular operator.

The user control device includes a user control part that is radially extendable and retractable relative to the medical system. The user control device makes flexible positioning of the user control part possible. In combination with the pivotability of the user control device, this makes free positioning of the user control part possible within an area on the floor.

The user control part can be positioned with little wear or noise by supporting the user control part on at least one wheel and/or on a sliding sheet. In combination with the aforementioned connecting bridge, wear from friction to the user control device can be avoided especially effectively.

In one embodiment, the user control part can be connected to a system component near the floor of the medical system by the connecting part. The entire user control device may be located close to the floor, where it is little hindrance to the operator.

The connecting part is supported on its underside on the system component near the floor. Supporting the connecting part via a swivel joint on the system component near the floor assures a structurally simple and stable construction. Disposing the system component near the floor makes it possible to protect the swivel joint from external influences.

In one embodiment, the user control part includes a disk at least partially filling an interstice below the system component near the floor. An accumulation of dirt in the interstice is avoided. The disk is a rotary disk that can be pivoted with the user control device. The rotary disk may, for example, be disposed on the swivel joint.

A user control part with a user control element part that is tiltable in two different directions makes an especially compact construction possible. The user control element can, for example, be a user control lever, similar to a joystick, which is tiltable in two directions perpendicular to one another. The one control lever, with its two different tilting directions, makes it possible to adjust two different parameters.

A user control part, as the at least one user control element, has a first switch and a second switch for selecting a function designation for the first switch. The user control part makes an especially compact construction possible. The user control part can be used to adjust a plurality of parameters with the first user control element, which is, for example, a rocker switch.

The user control device can control a medical system in the form of a mammography system. In a mammography system, it is especially important for the operator, such as a technician, to have his hands available for positioning the object being examined while the system parameters are being adjusted. In this positioning, mammography system cords on the floor are a particular hindrance. The user control device can be used in other radiological systems besides a mammography system as well.

In one embodiment, one or more of the following three system parameters can be controlled by the at least one user control element: a height of a stage of the mammography system, a spacing of a compression joint of the mammography system relative to its stage, and/or an imaging angle of a radiological unit, including the compression joint and an X-ray emitter, of the mammography system relative to a given object being examined. The height and spacing are adapted during the positioning of the object being examined on the stage, so that these system parameters can be adjusted unhindered, with one foot.

In one embodiment, a medical system includes at least one user control device of the aforementioned type provided for controlling the system.

The medical system is a mammography system. Disposing a user control device on the left and right relative to the patient on the floor plate of the mammography system easily makes especially good accessibility possible to at least one of the two user control devices from the left or right side of the patient. The operator can perform positioning of the object being examined from either the left or the right side of the patient while simultaneously operating one of the two user control devices.

BRIEF DESCRIPTION OF THE DRAWINGS

The present embodiments will be described in further detail below in terms of exemplary embodiments schematically shown in the drawings, without restricting the invention to these exemplary embodiments.

DETAILED DESCRIPTION

Figure 1:
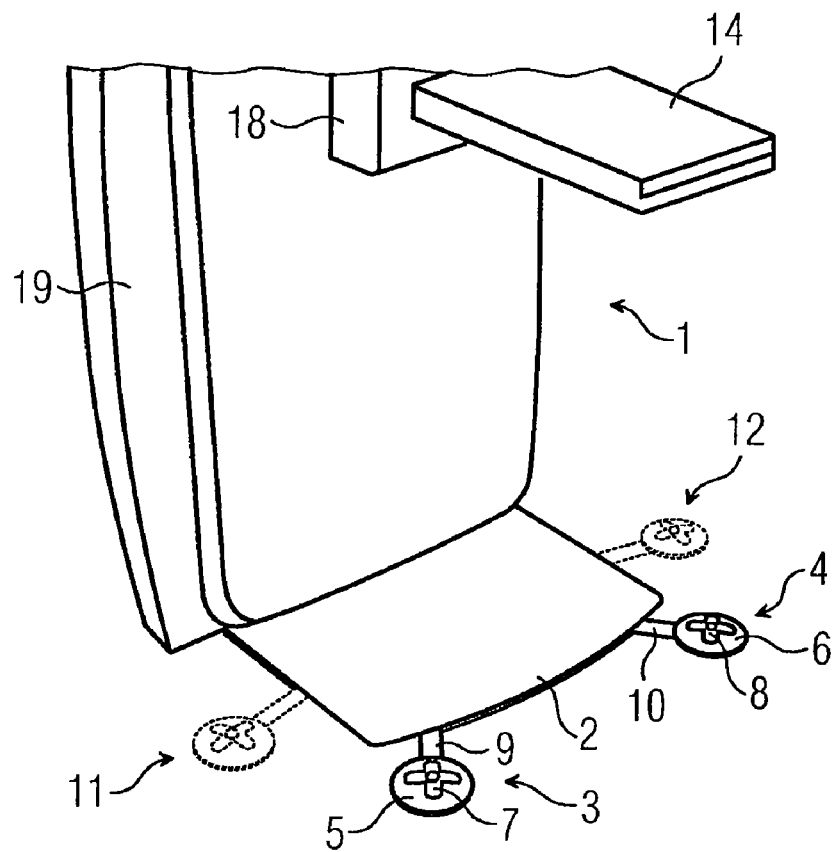
FIG. 1 illustrates a lower part of a mammography system and two user control devices, each with one user control part and one dimensionally stable connecting part between the user control part and the floor plate of the mammography system.

FIG. 1 shows a mammography system 1 with a floor plate 2, which includes a user control device 3 and 4. The control device 3 is disposed on the left and the control device 4 is disposed on the right. The user control devices 3 and 4 include user control parts 5 and 6, respectively. The user control parts 5 and 6 are supported near the floor. The user control parts 5 and 6 include at least one user control element 7 and 8, respectively, for controlling the mammography system 1. The user control parts 5 and 6 include dimensionally stable connecting parts 9 and 10, respectively, between the mammography system 1 and the respective user control part 5 and 6. The user control parts 5 and 6 are, together with their associated connecting parts 9 and 10, a one-piece unit and are made, for example, by injection molding from plastic. The connecting parts 9 and 10 include a hollow shaft of open cross section for receiving signal lines in the form of electrical cable connections.

In an alternative embodiment, one user control device may be disposed on the floor plate 2. If only one user control device is used, then the one user control device may be pivotable from the left side relative to the intended position of a particular patient to be examined.

The connecting parts 9 and 10 are located partly below the floor plate 2, where they are disposed pivotably, each about a vertical axis, on a swivel joint. The two swivel joints may, for example, be ball bearings. Because of the pivotable support, the user control devices 3 and 4 can be pivoted from their original position to a position shown in dotted lines. The operator of the mammography system 1 can position each of the user control parts 5 and 6 in such a way that good accessibility to his foot is assured.

Figure 2:
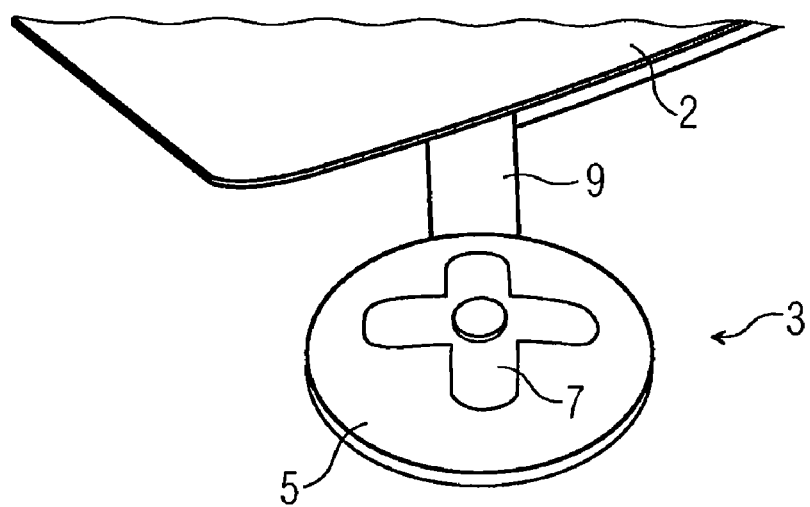
FIG. 2 illustrates one of the two user control devices shown in FIG. 1.

FIG. 2 shows the user control device 3 on the left along with the user control part 5 and the connecting part 9 of FIG. 1. The user control part 5 includes one user control element 7 for controlling system parameters of the mammography system 1. In this exemplary embodiment, the user control element 7 is a joystick, which is tiltable in two directions perpendicular to one another. By tilting the user control element 7 in one of the two directions, a height of a stage of the mammography system 1 is controllable. By tilting the user control element 7 in the other of the two directions, a spacing of a compression joint of the mammography system 1 relative to its stage is controllable. The two system parameters mentioned will be described hereinafter in conjunction with FIG. 3.

Below the user control part 5 there are two wheels, which make low-friction pivoting of the user control device 3 possible. The connecting part 9 is rigid and has a slight spacing from the floor, so that on being pivoted the connecting part 9 does not scrape over the floor. Low-friction pivoting of the user control device 3 would also be possible when the underside of the user control part 5 and the connecting part 9 have a slidable coating.

Figure 3:
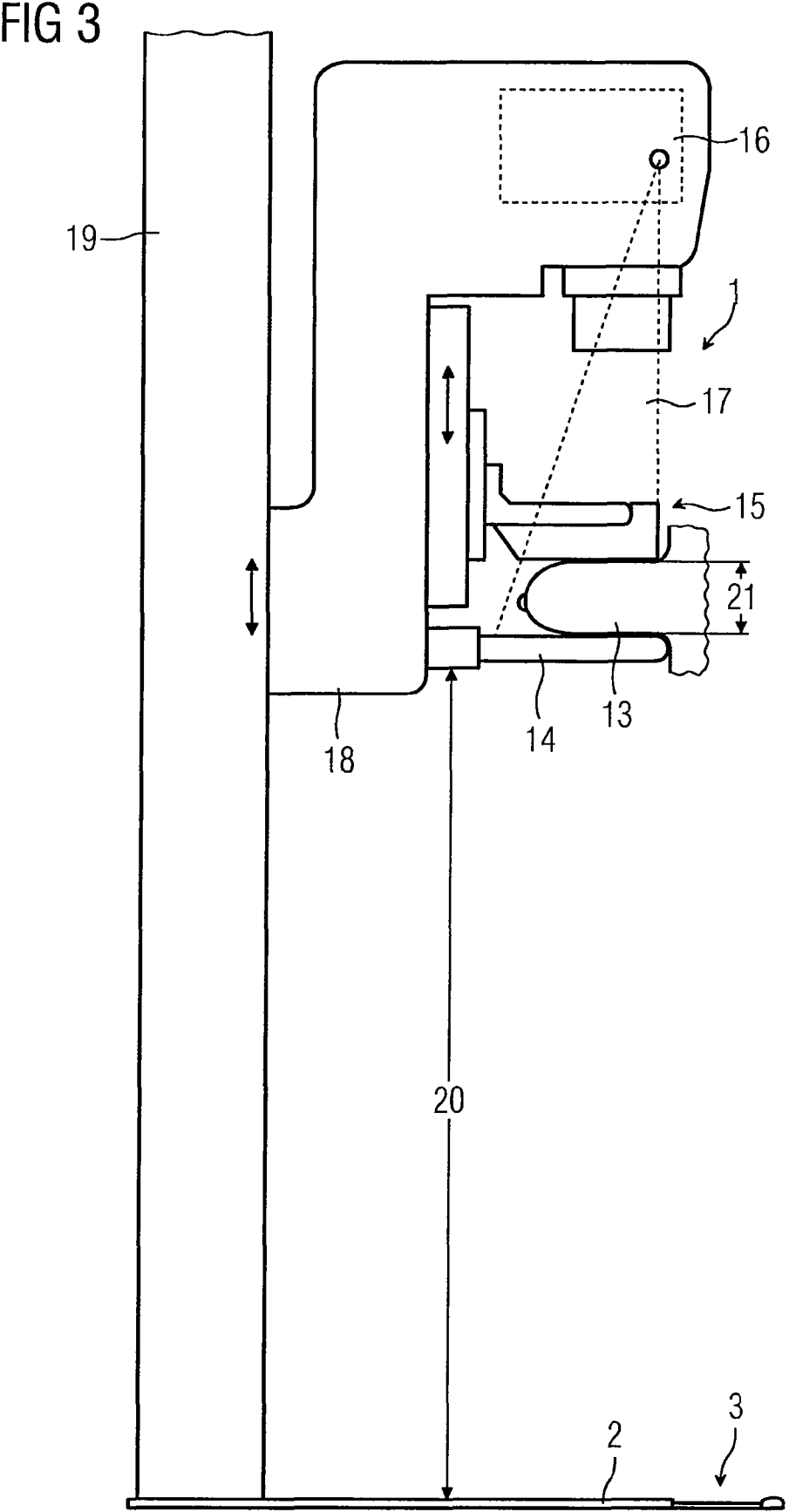
FIG. 3 illustrates a mammography system with an adjustable-height radiological unit with a stage and with a compression joint whose spacing from the stage is adjustable.

FIG. 3, in a side view, shows the upper half of the mammography system 1. An object being examined 13 is positioned on a stage 14 and is compressed by a compression joint (plate) 15. During examination, the object being examined 13 can be exposed to X-radiation 17 through an X-ray emitter 16. An image of the object being examined 13 is generated on an X-ray detector disposed in the stage 14.

For adaptation to the given object being examined 13, the X-ray unit 18, along with the X-ray emitter 16 of the compression joint 15 and with the stage 14 is adjustable in its height 20 relative to a tripod 19 of the mammography system 1. The compression joint 15 is adjustable in the spacing 21 from the stage 14. The adjustment of the aforementioned height 20 and the aforementioned spacing 21 can be done using the user control element 7 of the user control device 3. A rotation of the X-ray unit 18 about a horizontal axis may be controlled with the user control element 7, to vary the particular imaging angle for the X-ray examination. Accordingly, mediolateral-oblique (MLO) X-rays, for example, may be taken.

Figure 4:
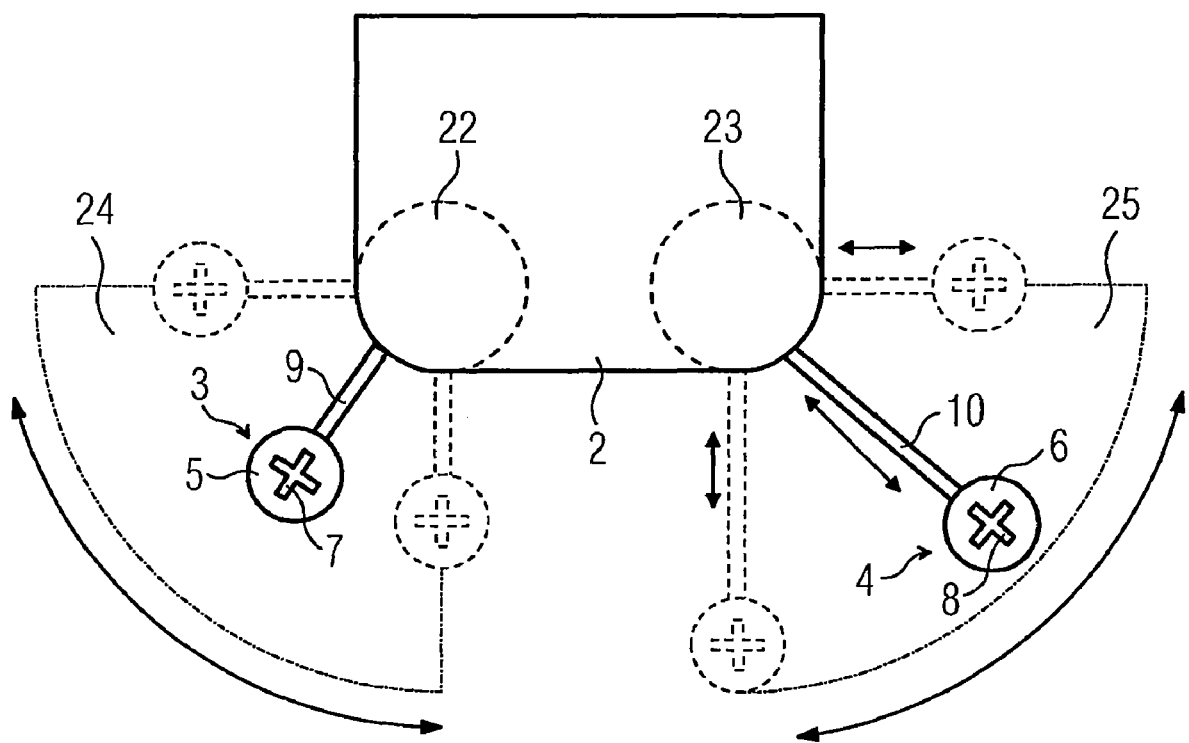
FIG. 4 illustrates a floor plate of a mammography system with two user control devices, which are supported pivotably and radially retractably and extendable below the floor plate.

FIG. 4 shows the floor plate 2 with the two user control devices 3 and 4 of FIG. 1. In this exemplary embodiment, the user control devices 3 and 4 are radially retractable and extendable. For the two user control devices 3 and 4, three different positions each are shown in the drawing. Pivoting and retracting and extending the user control devices 3 and 4 make them each movable within a range of motion 24 and 25, respectively, that is defined by structural provisions.

By way of the ranges of motion 24 and 25, the user control devices 3 and 4 can be pivoted and retracted and extended in a continuously variable fashion. Detent positions to be predetermined for the pivoting and the retraction and extension.

To enable the pivotability relative to the mammography system 1, a bearing is disposed on the end of the connecting part 9 and 10 remote from the respective user control part 7 and 8. Via these bearings, the connecting parts 9 and 10 can be supported pivotably on the floor plate 2 of the mammography system 1.

The swivel joints of the user control devices 3 and 4, in this exemplary embodiment, are disposed close to the front edge, on the side toward the patient, of the floor plate 2. The pivoting ranges of the connecting parts 9 and 10 below the floor plate 2 form one interstice in which dirt could accumulate. To avoid this kind of soiling, the interstices are each filled with a respective rotary disk 22 and 23, which each rotate along with the pivoting of the respective user control devices 3 and 4. The rotary disks 22 and 23 include a guide conduit for securely guiding the connecting parts 9 and 10 upon their retraction and extension. In the middle of each rotary disk 22 and 23 is a respective swivel joint, which rotatably connects the respective rotary disks 22 and 23 to the floor plate 2.

In one embodiment, a user control device includes a user control part that can be supported near the floor, with at least one user control element, for controlling a medical system should be operated with especially little wear and little hindrance by a dimensionally stable connecting part from the user control part to the medical system. An easily wearing cord that also hinders an operator need not be used for connecting the user control part. The operation of the medical system is possible with one foot, by actuation of the at least one user control element, so that the operator can use his hands for other handling actions. A disposition of the user control device such that it is pivotable and/or extendable and retractable relative to the medical system makes flexible positioning of the user control part possible, and this part in this way is especially readily accessible for equipment operation actions. The user control device of the invention is advantageously intended for the operation of a mammography system.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A user control device for controlling a medical system, comprising:
   a user control part, which is supported near the floor, with at least one user control element positioned and configured to be operated by foot to control the medical system,
   a dimensionally stable connecting part between the medical system and the user control part,
   wherein the user control part and the dimensionally stable connecting part are pivotable about a vertical axis relative to the medical system, and
   wherein the connecting part is supported on a connecting part underside on a system component near the floor via a swivel joint.

2. The user control device as defined by claim 1, wherein the connecting part includes at least one signal line for transmitting control signals from the at least one user control element to the medical system.

3. The user control device as defined by claim 2, wherein the at least one signal line is at least one electrical cable connection disposed inside the connecting part.

4. The user control device as defined by claim 2, wherein the connecting part is a hollow shaft that is operable to receive the at least one signal line.

5. The user control device as defined by claim 1, wherein the user control part and the connecting part are together a one-piece unit.

6. The user control device as defined by claim 1, wherein the connecting part is a connecting bridge that is at least partially spaced from the floor.

7. The user control device as defined by claim 1, wherein the user control part is operable to be extended or retracted relative to the medical system in the radial direction.

8. The user control device as defined by claim 1, wherein the user control part includes at least one wheel and/or on a sliding sheet that supports the user control part on the floor.

9. The user control device as defined by claim 1, wherein the system component near the floor is a floor plate of the medical system.

10. The user control device as defined by claim 9, wherein the user control device includes a disk that at least partially fills an interstice below the system component near the floor.

11. The user control device as defined by claim 1, wherein the at least one user control element is tiltable in two different directions.

12. The user control device as defined by claim 1, wherein the at least one user control element includes a first switch and a second switch for selecting a function designation for the first switch.

13. The user control device as defined by claim 1, wherein the user control device is operable to control a mammography system.

14. The user control device as defined by claim 13, wherein the at least one user control element is operable to control a height of a stage of the mammography system.

15. The user control device as defined by claim 14, wherein the at least one user control element is operable to control a spacing of a compression joint of the mammography system relative to the stage of the mammography system.

16. The user control device as defined by claim 15, wherein the at least one user control element is operable to control an imaging angle of an X-ray unit, which includes the compression joint and an X-ray emitter, relative to a given object being examined.

17. A medical system, comprising:
 a medical device; and
 at least one user control device that is operable to control the medical device,
 wherein the at least one user control device includes:
  a user control part, which is supported near a base of the medical device, with at least one user control element positioned and configured to be operated by foot to control the medical device, and
  a dimensionally stable connecting part between the medical device and the user control part, the user control part and the dimensionally stable connecting part being pivotable about a vertical axis relative to the medical device.

18. The medical system as defined by claim 17, wherein the medical device is a mammography system.

19. The medical system as defined by claim 18, wherein a first of the at least one user control devices is disposed on the left of a patient, and a second of the at least one user control devices is disposed on the right of the patient, the first and second user control devices being disposed on a floor plate of the mammography system.

20. The medical system as defined by claim 19, wherein the first and second user control devices are disposed in a corner, on the side toward the patient, of the floor plate.

\* \* \* \* \*